(12) United States Patent
Anders et al.

(10) Patent No.: US 7,755,763 B2
(45) Date of Patent: Jul. 13, 2010

(54) ATTENUATED TOTAL REFLECTION SENSOR

(75) Inventors: Klaus-Dieter Anders, Oberrohrdorf (CH); Martin Haller, Friedlisberg (CH)

(73) Assignee: Mettler-Toledo AG, Greifensee (CH)

( * ) Notice: Subject to any disclaimer, the term of this patent is extended or adjusted under 35 U.S.C. 154(b) by 93 days.

(21) Appl. No.: 12/110,752

(22) Filed: Apr. 28, 2008

(65) Prior Publication Data

US 2008/0309922 A1 Dec. 18, 2008

(30) Foreign Application Priority Data

Jun. 13, 2007 (EP) .................. 07110146

(51) Int. Cl.
*G01N 21/00* (2006.01)
(52) U.S. Cl. .............. 356/436; 356/246; 356/440
(58) Field of Classification Search ............. 356/73, 356/445, 447–448, 432–433, 436–437, 128–137, 356/246, 440, 133; 250/339.07, 339.08, 250/339.09
See application file for complete search history.

(56) References Cited

U.S. PATENT DOCUMENTS

| | | | | |
|---|---|---|---|---|
| 4,011,015 A | * | 3/1977 | Baba ...................... | 356/136 |
| 7,339,657 B2 | | 3/2008 | Coates | |
| 2004/0147034 A1 | * | 7/2004 | Gore et al. ................ | 436/95 |
| 2006/0197954 A1 | | 9/2006 | Ogura et al. | |
| 2007/0004030 A1 | | 1/2007 | Ogura et al. | |
| 2007/0082408 A1 | | 4/2007 | Jing et al. | |

FOREIGN PATENT DOCUMENTS

| | | |
|---|---|---|
| CH | 674082 A5 | 4/1990 |
| EP | 1630543 A1 | 3/2006 |

OTHER PUBLICATIONS

Nenninger, G.G. et al., "Reference-compensated biosensing using a dual-channel surface plasmon resonance sensor system based on a planar lightpipe configuration", Sensors and Actuators B, 1998, pp. 38-45, 51.
Reiter, G. et al., "In situ FTIR ATR spectroscopic study of the interaction of immobilized human tumor necrosis factor-α with a monoclonal antibody in aqueous environment", Biochimica et Biophysica Acta, 2004, pp. 253-261, 1699.

* cited by examiner

*Primary Examiner*—Tarifur Chowdhury
*Assistant Examiner*—Michael Lapage
(74) *Attorney, Agent, or Firm*—Standley Law Group LLP

(57) ABSTRACT

An attenuated total reflection ("ATR") sensor (3) determines a substance dissolved in a measurement medium (2). A method is taught to verify a calibration and/or to perform an in-line calibration of the sensor. The ATR sensor includes a housing (7) and an ATR body (4). A light source (12) and a detector (13) are arranged in the housing. The ATR body has at least one measurement surface (5) and, arranged parallel to the latter, a calibration surface (10). The measurement surface (5) can be brought into contact with the measurement medium. A calibration chamber (9), arranged in the housing, is delimited on at least one side by the calibration surface.

15 Claims, 2 Drawing Sheets

ATTENUATED TOTAL REFLECTION SENSOR

CROSS-REFERENCE TO RELATED APPLICATIONS

This application claims a right of priority under 35 USC §119 from European patent application 07110146.3, filed 13 Jun. 2007, the content of which is incorporated by reference as if fully recited herein.

TECHNICAL FIELD

The invention relates to an attenuated total reflection (ATR) sensor for the content determination of a substance dissolved in a measurement medium by means of the attenuated total reflection method, and it also relates to a method to verify the calibration and/or to perform an in-line calibration of the ATR sensor.

BACKGROUND OF THE ART

Attenuated total reflection (also referred to as attenuated total reflectance, abbreviated ATR) is a spectroscopic technique, whereby a sample is investigated by means of internal reflection. Electromagnetic radiation, for example radiation in the mid-infrared range, is coupled into an ATR body through a first cut surface and then reflected on a first surface. The radiation is reflected several times along the ATR body between said first and a second surface, wherein each reflection is an attenuated total reflection. One advantage of ATR spectroscopy is that already a very short optical path length is sufficient for the determination of a spectrum. The penetration depth of the radiation into the sample depends on the respective refractive indices of the sample and of the ATR body and on the angle of incidence at which the radiation meets the sample.

If a sample or a measurement medium is brought into contact with one of these surfaces, a part of the radiation is selectively absorbed by the sample at each reflection. The remaining radiation is coupled out of the ATR body at the other end, and the energy distribution of the radiation absorbed by the sample or measurement medium is registered by a detector. The energy distribution can be presented at the output as a function of the wavelength, i.e. as a spectrum, or the absorption is registered only for at least one wavelength. The known state of the art includes bodies of various shapes for the internal reflection. In many cases, the bodies are crystals that are optically transparent for the radiation that is used for the measurement.

ATR spectroscopy is used primarily in the laboratory for the investigation of samples of different kinds. A conventional ATR spectrometer has, besides the ATR body, a radiation source, a detector as well as suitable optical means for coupling the radiation into or out of the ATR body. The sample under investigation can be solid, liquid, or also gaseous.

Besides laboratory applications, other known uses include applications in chemical, biological or physical processes where for example by means of an ATR probe, a measurement medium is investigated which is brought into contact with a measuring surface of the ATR body. Especially in process applications it is often the case that not the entire spectrum is analyzed but that only selected wavelengths are coupled into the ATR body and/or detected, as a way to determine the absorption of specifically targeted substances that are present in the measurement medium and, in addition, to determine their concentration in the process- or measurement medium.

The determination of one or more dissolved substances in a medium, especially the determination of its content proportion or concentration is performed in the most diverse fields such as for example the beverage industry or the field of biotechnology. Examples of such substances are carbon dioxide ($CO_2$), methanol, ethanol, methane, as well as other chemical substances that are contained in a fluid process- or measurement medium, for example in an aqueous solution or the like. Most of all, an accurate knowledge of the $CO_2$ content is of interest for the beverage industry as a part of production control.

ATR sensors with different ATR bodies for in-line measurements are known, for example, from U.S. Pat. No. 7,339,657, which discloses in particular ATR bodies with different geometrical shapes or with a recess on the side facing the measurement medium, so that the measurement medium can be examined with a combination of ATR-and transmission spectroscopy.

A known problem in spectroscopic examinations under process conditions presents itself in calibrating the sensor and in particular checking the calibration, and in performing the initial calibration and/or the recalibration of a sensor that is installed in a process system.

The relationship between the absorption and the concentration of a substance is established through Lambert-Beer's law which, for small concentrations, expresses a linear relationship between the two quantities.

However, if an individual substance or class of substances is to be determined in a complex measurement medium, the problem presents itself that frequently the radiation introduced into the ATR body is absorbed not only by the substance dissolved in the measurement medium but also by the measurement medium itself. Effects of this kind, among others, are referred to as matrix effects.

To minimize matrix effects, the calibration of a process-capable ATR sensor includes not only the measurement of different pure substances but in particular the concentration-dependent measurement of such substances in a measurement medium which may in some cases change its composition. Especially with measurement media of changing composition, for example media of the kind that are present during a beer-brewing process, it would be necessary for a full calibration that all combinations of measurement medium and substance content be measured and taken into account in the calibration, which is most of all very time-consuming.

A calibration of this kind is therefore often performed outside of the process with standardized samples and reflects the actual process conditions only with a certain error tolerance.

To ensure the measurement tolerances and/or the correct functioning of ATR sensors, in particular those which are installed in a process system and are used for the examination of measurement media which are of the same kind or are subject to change, it would be advantageous to have the capability to determine and/or verify the calibration of the sensor in the installed or in-line condition.

SUMMARY OF THE INVENTION

This task is solved by an ATR sensor for the determination of a substance dissolved in a measurement medium and by a method for the calibration of the sensor.

The ATR sensor has an ATR body and a housing and, arranged in the latter, a light source and a detector. The ATR body, in turn, has at least one measurement surface and a calibration surface arranged parallel to the measurement surface, wherein the measurement surface can be brought into contact with the measurement medium and the calibration surface forms the border of a calibration chamber on at least one side, said calibration chamber being arranged inside the housing.

A sensor of this kind allows a calibration standard to be introduced into or to be removed from the calibration chamber and to be measured while the sensor is in the installed state in the process system and is in contact with the measurement medium, which makes it possible to check an initial calibration that was performed for example at the factory or even to perform an in-line calibration, i.e. a calibration of a sensor that is installed in a process system.

In a preferred embodiment, a radiation emitted by the light source can be coupled into the ATR body and subsequently reflected alternatingly at the measurement surface and at the calibration surface. In this way, an absorption value can be determined which includes the absorption of the measurement medium that is in contact with the measurement surface as well as the absorption of the calibration standard that is in contact with the calibration surface.

On the side that faces away from the medium, the ATR body is preferably designed to have at least one recess which is delimited on one side by the calibration surface. By closing off this recess with suitable means, the calibration chamber can be formed.

This arrangement is advantageous because it makes a direct contact possible between the calibration surface and a calibration standard arranged in the calibration chamber.

The calibration chamber preferably has at least one connection to carry a fluid calibration standard in and/or out, which makes it possible to use different calibration standards. The term "calibration standard" as used here is also meant to include reference media, so that it is not only possible to perform a calibration but also to make a measurement of measurement medium and reference medium. Further, the word "fluid" as used here is understood to mean a readily flowing medium, whether liquid or gaseous. If a reference medium is used, the absorption value to be determined includes the absorptions of the reference medium and of the measurement medium.

The ATR sensor is distinguished in that it is formed monolithically of one piece or of component bodies that are solidly connected by means of an optically transparent material. ATR bodies can consist of different materials including, among others, diamond, sapphire, cadmium telluride, thallium bromide iodide, silicon, germanium, zinc selenide, zinc sulfide, magnesium fluoride, cesium chloride, silver chloride, calcium fluoride, potassium bromide, coated sodium chloride, as well as polymers such as polyethylene, and related optically transparent substances.

Preferably, the ATR body comprises a hollow cylinder which includes the recess, and a truncated cone which caps the hollow cylinder and whose base has the same diameter as the hollow cylinder. Further design configurations include for example an embodiment with a substantially U-shaped ATR body with straight edges, wherein the recess in the ATR body has to be closed off on three sides by suitable walls in order to form a calibration chamber.

A further aspect of the invention includes a method to check the calibration and/or to perform an in-line calibration of an ATR sensor for a substance dissolved in a measurement medium, in particular for a sensor of the kind described above which includes an ATR body, at least one light source and at least one detector. While the checking and/or the in-line calibration takes place, the sensor can remain in the process.

To perform a calibration, a measurement surface of the ATR body is brought into contact with the measurement medium, and a first absorption value is measured for at least one wavelength. The absorption value is measured by means of the detector after the attenuated total reflection of a radiation injected by a light source into the ATR body.

The term "absorption value" in the present context means the absorption at a specific wavelength, or a value determined from the absorptions spectrum within a specific range of wavelengths, which is taken as a measure for the absorptance of the substance at this wavelength or in this range of wavelengths.

As a next step, a calibration surface of the ATR body that is arranged parallel to the measurement surface can be brought into contact with a first fluid calibration standard, wherein the first calibration standard is present in the calibration chamber in a first concentration. Frequently, the chemical composition of the calibration standard corresponds essentially to the substance to be examined, which is dissolved in the measurement medium, or it is a pure substance with a characteristic absorption band or a characteristic absorption spectrum.

At this point, a second absorption value can be measured at the same wavelength or wavelengths, which represents a superposition of the respective absorptions of the measurement medium and the calibration standard. The radiation emitted by the light source is reflected alternatingly at the measurement surface and at the calibration surface which is parallel to the measurement surface and interacts with the measurement medium as well as with the calibration standard.

Based on the first and second absorption values, with the concentration or content of the first calibration standard being known, and assuming Lambert-Beer's Law to be applicable, it is possible to determine a calibration-checking function. Lambert-Beer's law shows a linear relationship between the concentration and the absorption of a substance or sample, so that based on two measurement data points a two-point calibration can be performed. The first measurement data point corresponds in this case to the first absorption value which was measured with a substance concentration set at zero, and the second measurement data point corresponds to the second absorption value and to the concentration of the calibration standard.

The calibration-checking function determined in this manner can be compared to an initial calibration of the kind performed for example at the factory or outside of the process. If the checking function and the initial calibration are essentially in agreement with each other, one can continue to use the initial calibration for the determination of the measurement values. If the checking function deviates from the initial calibration, this indicates that the sensor should be recalibrated.

To determine a new or current calibration function, at least a second calibration standard with a second concentration can be brought into contact with the calibration surface, and a third absorption value can be determined. This third absorption value includes the absorption of the second calibration standard as well as of the measurement medium.

The current calibration function can be determined on the basis of the same assumptions as the calibration-checking function, but taking into account the first, second and third absorption values and the first and second concentrations of the calibration standard. The updated calibration function can thus be determined by a three-point calibration. Instead of evaluating individual absorption values using in particular linear regression methods, one could also evaluate the entire absorption spectrum. Methods that are suitable for this task include primarily the chemometric techniques such as multiple linear regression or partial least-square analysis.

The checking of the calibration and/or the in-line calibration can of course also be repeated in regular time intervals and/or at times set by the user in order to verify the quality of the measurement results.

The composition of the measurement medium should preferably remain unchanged during the time period when the calibration is being checked and or while the in-line calibration is taking place, because otherwise absorption values will be set in correlation with each other which have different matrix effects.

The calibration standard is frequently a fluid medium and preferably a gaseous medium. Through suitable conduits or inlets the calibration standard can be introduced into, or removed from, a calibration chamber which is delimited on one side by the calibration surface.

In the case of a gaseous calibration standard, the concentration or content of the calibration standard in the calibration chamber can be adjusted by way of its partial pressure.

In addition to measuring an absorption value at a first wavelength, it is possible to simultaneously determine an absorption value at a measurement wavelength and a further absorption value at a calibration wavelength that is different from the measurement wavelength. By way of the absorption coefficient, Lambert-Beer's law also entails a dependency on the wavelength, so that by simultaneously determining the absorption values at different wavelengths it becomes possible to determine two calibration-checking functions and/or at least two current calibration functions associated with the respective wavelengths, to gain better control over matrix effects, and/or to even perform a measurement and a calibration check in parallel.

For a simultaneous measurement of the absorption values at more than one wavelength, the light source should either consist of a plurality of light sources, each emitting radiation of a specific wavelength, or emitting radiation of a specific range of wavelengths such as so-called broad-band light sources. The detector should likewise have the capability to simultaneously detect a plurality of wavelengths or a range of wavelengths. ATR spectroscopy investigations can be performed in different ranges of wavelengths, with the mid-infrared range being particularly suitable, because many molecules show characteristic absorption bands in this range.

If ATR sensors are used to determine the content of carbon dioxide dissolved in a liquid measurement medium, one can use for example a measurement wavelength of about 4.24 μm and a calibration wavelength of about 3.95 μm, as carbon dioxide has absorption bands at both of these wavelengths. Depending on the measurement medium in which a substance is dissolved, the midpoint of an absorption band can shift, so that the wavelength data should be taken more in the sense of guide values. These effects have long been known in the field of optical spectroscopy.

Besides $CO_2$ oscillations it is also possible to detect CH oscillations at about 3.4 μm and CO oscillations at about 9.5 μm and to thereby determine the content in the measurement medium for substances that include molecules or molecule fragments with CH— and/or CO bonds.

It suggests itself to implement the foregoing method as a computer program in a processing unit of an ATR sensor according to the invention, wherein the computer program serves in particular to determine a measurement result, such as the content or the concentration of a dissolved substance, by means of an initial calibration or a current calibration, and/or to verify a calibration.

BRIEF DESCRIPTION OF THE DRAWINGS

An ATR sensor according to the invention is described in more detail in the following drawing figures, wherein features that are the same from one drawing to another are identified with the same reference symbols, and wherein.

DETAILED DESCRIPTION OF THE PREFERRED EMBODIMENTS

Figure 1:
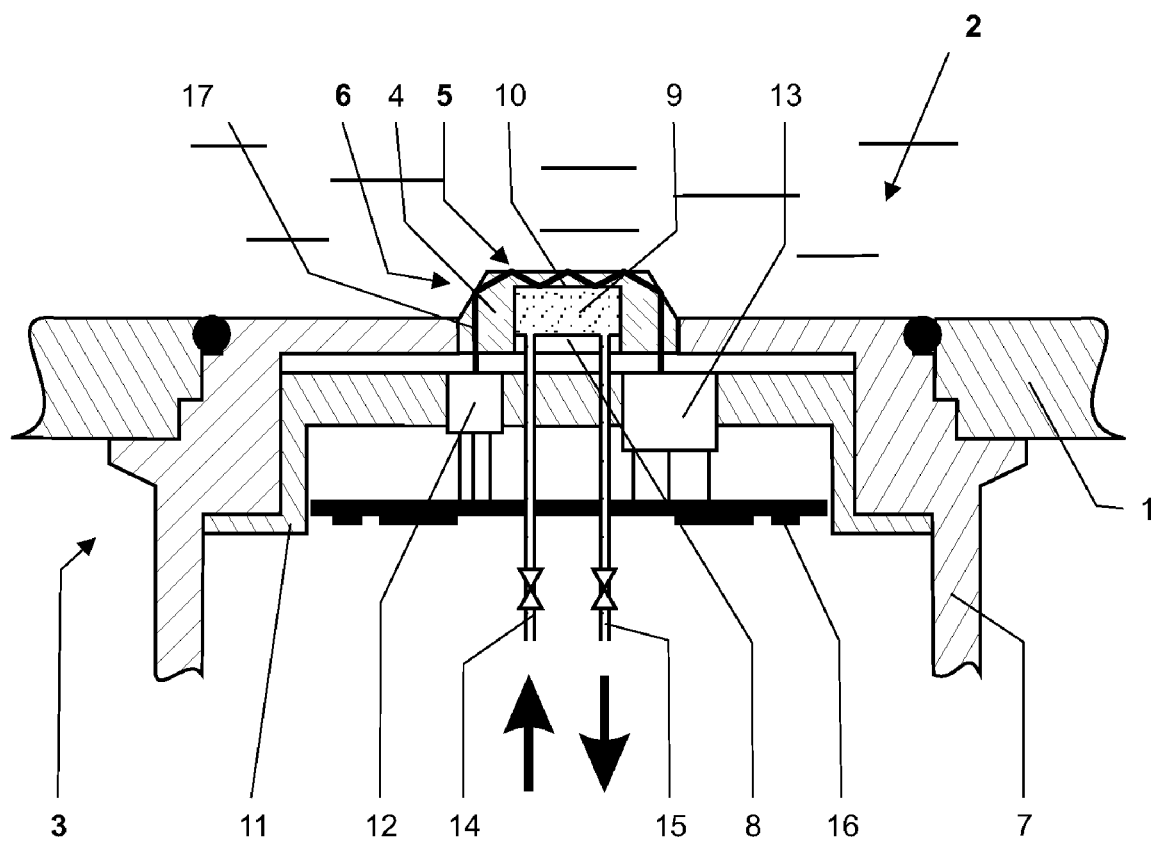
FIG. 1 is a sectional view of an ATR sensor which is in contact with a measurement medium, and FIG. 2 schematically illustrates a detail of FIG. 1.

FIG. 1 shows an ATR sensor 3 which is installed in a process system or in a container indicated here by a container wall 1. A fluid measurement medium 2 in which the substance to be examined is dissolved is present in the system. Fluid measurement media can be liquid and/or gaseous. Dissolved substances that can be investigated with an ATR sensor include for example substances such as carbon dioxide, carbon monoxide or compounds containing hydrocarbons, but it should be understood that other substances can likewise be measured as long as they exhibit characteristic absorption lines and the sensor includes appropriately adapted components.

The core of the sensor 3 is an ATR body 4 with a measurement surface 5 which is in direct contact with the measurement medium 2. The ATR body 4 shown here includes in essence a hollow cylinder which is capped by a truncated cone, wherein the outside diameter of the hollow cylinder and the diameter at the base of the truncated cone are essentially equal (also see FIG. 2). The ATR body 4 can be made monolithically of one piece, or of several component pieces which are joined together with an optically transparent connecting agent. If a sapphire crystal is used as ATR body, it can be soldered into a housing 7 by means of a suitable solder material, for example gold- or platinum solder. ATR bodies made of other materials can also be arranged in the housing 7 by means of suitable sealing agents, so that a connection that is impermeable to a medium and is preferably gas-tight is formed between the ATR body 4 and the housing 7. One surface, the measurement surface 5, as well as the lateral circumference wall 6 of the ATR body 4 can be brought into direct contact with the measurement medium 2.

On the side facing towards the measurement medium 2, the housing 7 has a process flange whereby the sensor 3 is fastened to a process system or to another container, as indicated here by the wall 1.

On the side facing away from the measurement medium 2, the ATR body 4 has a recess 8 which is configured at least in part as a calibration chamber 9. The recess 8 has an essentially round cross-section, and is delimited on the side towards the measurement medium 2 by a planar calibration surface 10 which runs parallel to the measurement surface 5. Towards the interior of the sensor 3 the calibration chamber 9 is preferably sealed gas-tight and has two conduits 14, 15 to let a fluid calibration standard flow in and/or out. The conduits 14, 15 are connected for example to a reservoir and/or to a vacuum pump (neither of them shown here), so that the calibration standard can be brought into or removed from the calibration chamber 9.

To perform a calibration, the fluid calibration standard is conducted into or through the calibration chamber in different concentrations or, in the case of gaseous standards, with different partial pressures. For each concentration a separate absorption value is measured which can be used for an internal calibration or to check an initial calibration. The calibration standard frequently contains the same substance or the principal component of the same substance as the one being measured. For a description of the ATR body 4, the reader is also referred to FIG. 2.

In its interior the sensor 3 further contains a holder 11 to which a light source 12 as well as a detector 13 are attached. The radiation 17 emitted by the light source 12 is coupled by way of suitable optical elements into the ATR body and reflected first at the lateral surface 6. Further reflections occur alternatingly at the measurement surface 5 and at the calibration surface 10 until the radiation is directed out of the ATR body 4 again onto a detector 13. Each of the reflections is an attenuated total reflection. With each reflection at a surface, the radiation 17 penetrates the respective border surface separating the ATR body 4 from the measurement medium 2 on one side and/or from the calibration standard in the calibration chamber 9 on the other side, where part of the radiation is absorbed. The absorption detected by the detector 13 is thus composed of the absorption of the measurement medium 2 and the absorption of the calibration standard, provided that a calibration standard is present in the calibration chamber 9. The light source 12 as well as the detector 13 are connected through appropriate means to a control- and/or regulating unit 16 which can be arranged inside the sensor 3, as shown here, and/or at an external location.

Figure 2:
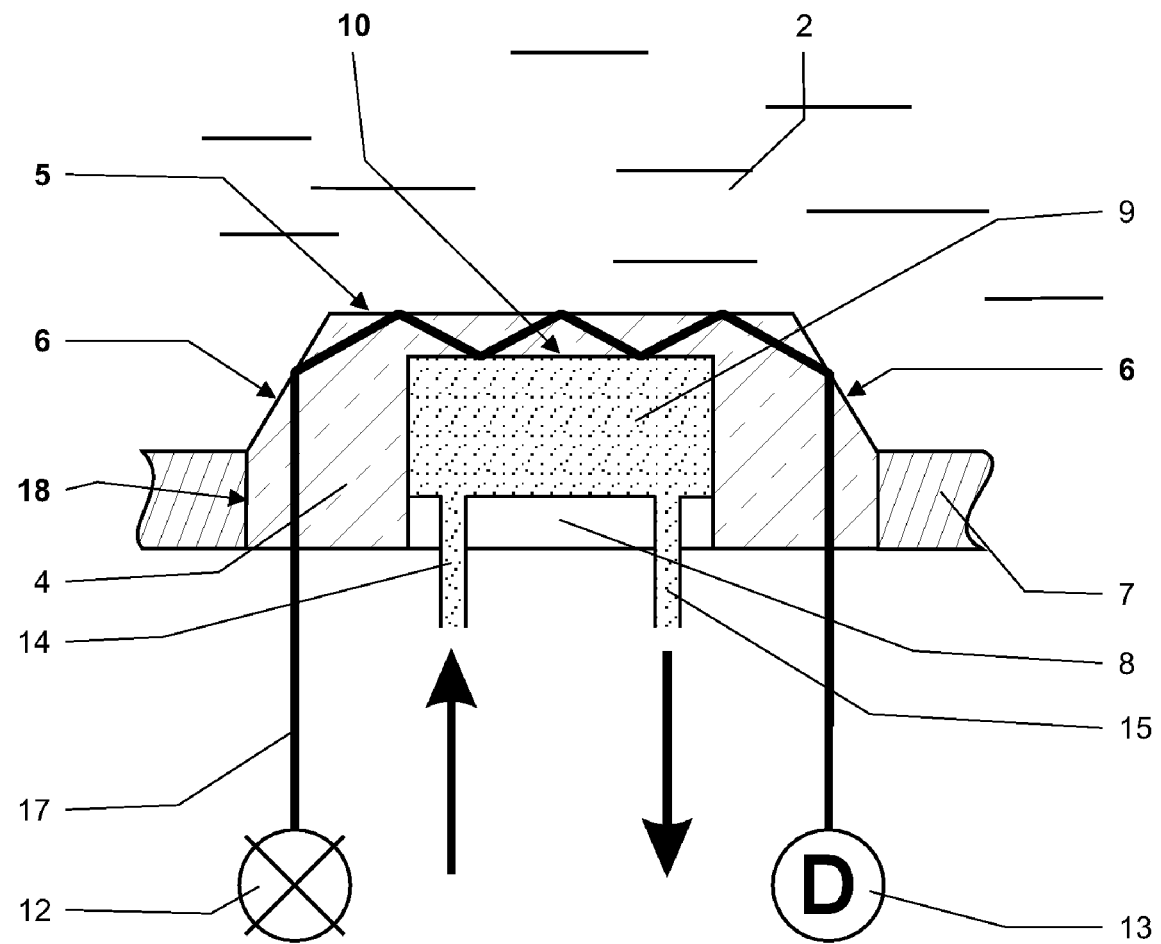

FIG. 2 schematically illustrates the ATR body 4 with the calibration chamber 5 as well as a possible light optical path 17 through the ATR body 4 as an enlarged detail of FIG. 1, shown in sectional view. The ATR body 4 is set into a sensor housing 7 in such a way that a preferably gas-tight connection is formed between the two components. This is accomplished for example by soldering into place an ATR body 4 consisting of sapphire or by using suitable sealing means.

The ATR body 4 has in essence the shape of a truncated cone which caps the cavity of a hollow cylinder. A measurement surface 5 of the ATR body 4 is surrounded by a slanted lateral surface 6 which continues into an area with an exterior surface 18 oriented perpendicular to the measurement surface 5. The exterior surface 18 is in contact with the sensor housing 7 through a sealing means such as for example a metallic solder material or an O-ring seal. On its inside, the ATR body 4 has a recess 8 which is open towards the interior of the housing 7. The recess 8 is delimited towards the measurement medium 2 by a calibration surface 10 which runs parallel to the measurement surface 5.

The side of the recess 8 that faces away from the measurement medium is closed off gas-tight by appropriate means, so that a calibration chamber 9 is created. The calibration chamber 9 as shown here has two conduits 14, 15 to carry fluid, in particular gaseous, calibration standards in and out as indicated by the arrows. The calibration chamber 9 can extend over part of the recess 8, as shown here, or also over the entire recess 8.

FIG. 2 further illustrates the light optical path 17. Through an appropriate optical arrangement (not shown), the radiation 17 is coupled from the light source 12 into the ATR body 4. The light source 12 can be designed as a narrow-band or broad-band light source. Narrow-band light sources are for example lasers, laser diodes, or also broad-band light sources from which a specific narrow spectral range is selected by means of interposed filters. Broad-band light sources used in ATR-MIR spectroscopy (where MIR stands for mid-infrared) include for example the so-called black-body radiators.

The radiation 17 enters into the ATR crystal 4 and falls first on the lateral surface 6 where an attenuation and total reflection occurs, so that the radiation 17 falls next on the measurement surface 5. After multiple total reflections which take place alternatingly at the measurement surface 5 and at the calibration surface 10, and after a final reflection on the lateral surface 6, the radiation 17 is coupled out again from the ATR body 4 and directed to the detector 13.

The detector 13 is matched to the radiation being used. Depending on the field of application, it is therefore possible to use a detector which covers the complete MIR range or a detector which can selectively detect at least one wavelength. For the detection of dissolved carbon dioxide one can use for example pyroelectric detectors, PbSe detectors, or so-called thermopiles.

To perform a measurement, the fluid calibration standard is removed from the calibration chamber 9, and the latter is either set under vacuum or filled with a gas or a gas mixture that is transparent or only weakly absorbent for the radiation being used.

As an alternative, it is also possible to bring a reference medium into the calibration chamber and to measure the measurement medium against the reference medium.

To perform a calibration or to check a current calibration or an initial calibration, different concentrations of the calibration standard are successively introduced into the calibration chamber 9. For a calibration check, the calibration standard is measured in at least one concentration. To perform an in-line calibration, measurements are made with at least two different concentrations of the calibration standard, wherein in each case a measurement made under identical conditions for the measurement medium without the calibration standard is used as zero point or base value.

While the procedure according to the method is carried out, the sensor remains in the measurement medium 2 and thus in the process system or in the container.

The detected absorption band or -bands, or the detected absorption spectrum, represents a superposition of the respective absorptions of the measurement medium and of the calibration standard, if the latter is present in the calibration chamber. By changing the concentration or the partial pressure of the fluid calibration standard in the calibration chamber and performing measurements with at least two concentrations, the in-line calibration described above can be carried out, or an initial calibration can be checked without the need to remove the sensor from the process.

What is claimed is:

1. A sensor for using attenuated total reflection of a radiation to determine a substance dissolved in a measurement medium, compared to a calibration standard, the sensor comprising:
    a housing comprising a light source for the radiation and a detector; and
    an ATR body, arranged between the light source and the detector for passage of the radiation therethrough, the ATR body comprising:
        a measurement surface in direct contact with the measurement medium; and
        a calibration surface in direct contact with the calibration standard and arranged-parallel to the measurement surface for alternating attenuated total reflections of the radiation at the respective measurement and calibration surfaces, the calibration standard contained in a calibration chamber arranged inside the housing, the calibration surface delimiting the calibration chamber on at least one side thereof.

2. The ATR sensor of claim 1, further comprising:
    a means for determining an absorption value that includes the absorption due to the measurement medium and the absorption due to the calibration standard.

3. The ATR sensor of claim 2, wherein:
the calibration chamber is formed by at least one recess on the side of the ATR body facing away from the measurement medium, the recess being delimited by the calibration surface and being closed off by suitable means.

4. The ATR sensor of claim 3, wherein:
the calibration chamber comprises at least one connection serving to introduce and/or to remove the calibration standard.

5. The ATR sensor of claim 4, wherein:
the ATR body is formed monolithically of one piece or of component bodies that are solidly connected by means of an optically transparent material.

6. The ATR sensor of claim 5, wherein:
the ATR body comprises:
  a hollow cylinder which includes the recess; and
  a truncated cone which caps the hollow cylinder, the truncated cone having a base with the same diameter as the hollow cylinder.

7. The ATR sensor of claim 1, wherein:
the calibration chamber is formed by at least one recess on the side of the ATR body facing away from the measurement medium, the recess being delimited by the calibration surface and being closed off by suitable means.

8. The ATR sensor of claim 1, wherein:
the calibration chamber comprises at least one connection serving to introduce and/or to remove the calibration standard.

9. The ATR sensor of claim 1, wherein:
the ATR body is formed monolithically of one piece or of component bodies that are solidly connected by means of an optically transparent material.

10. A method for checking the current calibration and/or performing an in-line calibration of an ATR sensor for a substance dissolved in a measurement medium, comprising the steps of:
  providing an ATR sensor including a housing comprising a light source and a detector, and an ATR body comprising a measurement surface, adapted to be brought into direct contact with the measurement medium, and a calibration surface, arranged parallel to the measurement surface and adapted to be brought into contact with a calibration standard contained in a calibration chamber arranged inside the housing, the calibration surface delimiting the calibration chamber on at least one side thereof;
  bringing the measurement surface of the ATR sensor into contact with the measurement medium;
  coupling a radiation from the light source into the ATR body;
  registering at least one first absorption value for at least one wavelength after attenuated total reflection of the radiation in the ATR body;
  bringing the calibration surface of the ATR sensor into contact with a first calibration standard which is present in a first concentration;
  registering at least one second absorption value that includes the absorption due to the measurement medium and the absorption due to the first calibration standard;
  determining a calibration-checking function based on the first and second absorption values and the concentration of the first calibration standard; and
  establishing a new current calibration by at least one of:
    comparing the calibration-checking function to the current calibration; and
    performing an in-line calibration by:
      bringing the calibration surface of the ATR sensor into contact with a second calibration standard with a concentration different from the first concentration;
      registering at least one third absorption value that includes the absorption due to the measurement medium and the absorption due to the first second standard; and
      determining an actual calibration function based on the first, second and third absorption values and the first and second calibration standards.

11. The method of claim 10, wherein:
each calibration standard is a fluid medium which is introduced into or removed from the calibration chamber.

12. The method of claim 10, wherein:
the absorptions of the calibration standard and of the measurement medium are measured for at least one measurement wavelength and at least one calibration wavelength, so that at least two calibration-checking functions and/or at least two current calibration functions can be determined dependent on the two wavelengths.

13. The method of claim 10, further comprising the step of:
determining the content of the substance in the measurement medium from the first absorption value using the current calibration.

14. The method of claim 10, wherein:
each of the registering steps comprises the substep of reflecting in an alternating manner a radiation emitted by the light source from the measurement surface and the calibration surface.

15. A processing unit containing a computer program on a computer readable medium and carrying out the method according to claim 10 on an ATR sensor to which the processing unit is connected, in particular for the determination of a measurement result by means of an initial calibration or a current calibration and/or to verify a calibration.

* * * * *